United States Patent
Huang et al.

(10) Patent No.: US 10,695,457 B2
(45) Date of Patent: Jun. 30, 2020

(54) ANTISEPTIC WOUND DRESSING

(71) Applicant: NAN LIU ENTERPRISE CO., LTD., Kaohsiung (TW)

(72) Inventors: Shih-Chung Huang, Kaohsiung (TW); Shang-Yuan Huang, Kaohsiung (TW)

(73) Assignee: NAN LIU ENTERPRISE CO., LTD., Kaohsiung (TW)

(*) Notice: Subject to any disclaimer, the term of this patent is extended or adjusted under 35 U.S.C. 154(b) by 0 days.

(21) Appl. No.: 16/449,432

(22) Filed: Jun. 23, 2019

(65) Prior Publication Data

US 2020/0000956 A1  Jan. 2, 2020

(30) Foreign Application Priority Data

Jun. 27, 2018 (TW) .............................. 107122142 A

(51) Int. Cl.
| | |
|---|---|
| *A61L 15/32* | (2006.01) |
| *A61F 13/00* | (2006.01) |
| *A61L 15/44* | (2006.01) |
| *A61L 15/58* | (2006.01) |

(52) U.S. Cl.
CPC ........ *A61L 15/32* (2013.01); *A61F 13/00063* (2013.01); *A61F 13/00991* (2013.01); *A61F 2013/0091* (2013.01); *A61F 2013/00931* (2013.01); *A61L 15/44* (2013.01); *A61L 15/58* (2013.01); *A61L 2300/104* (2013.01)

(58) Field of Classification Search
None
See application file for complete search history.

(56) References Cited

U.S. PATENT DOCUMENTS

| | | | |
|---|---|---|---|
| 2015/0367024 A1* | 12/2015 | Laukkanen | ............. A61L 15/28 424/444 |
| 2016/0082141 A1* | 3/2016 | Rogers | .................. A61L 15/225 602/48 |

\* cited by examiner

*Primary Examiner* — Nannette Holloman
(74) *Attorney, Agent, or Firm* — Leong C. Lei

(57) ABSTRACT

The antiseptic wound dressing includes at least nanometer chitin, alkaline earth metal alginate, and an antiseptic material. The nanometer chitin is tubular shaped having diameter 10~50 nm and length 20~200 nm. The amount of the nanometer chitin is 0.1%~5% to the alkaline earth metal alginate. The antiseptic wound dressing is manufactured by mixing nanometer chitin and alkaline metal alginate, further mixing with antiseptic material, conducting a wet spinning process to produce fibers, and conducting a non-woven cloth process to obtain the antiseptic wound dressing of the present invention. Therefore, the antiseptic wound dressing is capable of reducing the chance of would infection, and providing superior moisture retention and enhanced wet strength.

2 Claims, 2 Drawing Sheets

ANTISEPTIC WOUND DRESSING

BACKGROUND OF THE INVENTION

(a) Technical Field of the Invention

The present invention is generally related to antiseptic wound dressing, and more particular to an antiseptic wound dressing using nanometer chitin.

(b) Description of the Prior Art

Scientists have already confirmed from clinical experiments that ordinary wounds heal faster under a moist condition, thereby establishing the concept of occlusive dressing. Then, dressings using PU film, chitosan, collagen, alkaline earth metal alginate (alginate), or other natural material are developed. On the other hand, ordinary wound dressing may be made of non-woven cloth, film, or sponge. For example, British company Britcair's Kaltostat product is made of non-woven cloth.

There are acute wounds and chronic wounds. Acute wounds are often caused by external forces, such as bruises, incised wounds. Chronic wounds are often caused by the patients' weak immune system and the wounds are infested with vast amounts of bacteria, affecting the healing of the wounds. To overcome this problem, antiseptic material is added to the dressing to help healing the wounds.

The alginic acid for making the alkaline earth metal alginate wound dressing is mainly extracted from algae, and is a polymer compound composed of β-D-mannuronic acid and α-L-guluronic acid). Conventionally, non-woven wound dressing using alkaline earth metal alginate is manufactured as follows. A solution having 5% sodium alginate is first obtained. The sodium alginate solution is then run through a calcium chloride solution through spinneret to form fibers, which is further stretched and dried to obtain calcium alginate fibers. After opening, combing, and needle-bonding calcium alginate fibers, the calcium alginate non-woven dressing is achieved. To add antiseptic material, it is included when forming the sodium alginate solution. Finally, after wet spinning and non-woven processes, the antiseptic calcium alginate dressing is obtained.

Conventional antiseptic dressings usually include antiseptic materials, such as silver, Polyhexamethylene Biguanide (PHMB), or Chlorhexidine Gluconate (CHG). The purpose is to reduce bacteria around the wounds. However, antiseptic material may also adversely affect wound healing, as the antiseptic material may irritate normal cells and cause wound inflammation. The added antiseptic material also may often reduce the strength of the dressing.

Therefore, using silver-included wound dressing as example, its released silver ions indeed may kill bacteria but may also lead to cytotoxicity, affecting the healing of the wound. Secondly, calcium alginate fibers would have inferior strength due to the added silver particles. The dressing may be easily broken under the influence of body fluid, causing user inconvenience. Thirdly, fibers' moisture retention capability, which is vital to keep the wound moist, may also reduce due to the added silver particle.

As described above, antiseptic material, despite that it may kill bacteria, may also adversely affect wound healing, as the antiseptic material may irritate normal cells and cause wound inflammation. The added antiseptic material also often reduces the strength of the dressing. Therefore, there is ample room for improvement for antiseptic wound dressings.

SUMMARY OF THE INVENTION

In order to obviate the shortcomings of the conventional antiseptic wound dressing, the present invention teaches a novel antiseptic wound dressing with nanometer chitin added to enhance the dressing's capability in preventing wound infection and strength.

The antiseptic wound dressing of the present invention includes at least nanometer chitin, alkaline earth metal alginate, and an antiseptic material. The nanometer chitin is tubular shaped having diameter 10~50 nm and length 20~200 nm, and the amount of the nanometer chitin is 0.1%~5% to the alkaline earth metal alginate. The antiseptic material may include silver particles, Polyhexamethylene Biguanide (PHMB), or Chlorhexidine Gluconate (CHG). The antiseptic would dressing is manufactured as follows:

Step A: providing a first solution where nanometer chitin is dispersed evenly in water and alkaline metal alginate powder is mixed in the water;

Step B: providing a second solution by mixing an antiseptic material in the first solution;

Step C: conducting a wet spinning process, where the second solution is filled into a grooving tank storing a grooving liquid which includes 5% calcium chloride solution, when the second solution contacts with the calcium chloride solution, the sodium ions in the alkaline metal alginate swap with calcium ions to form solid fibers of calcium alginate, and the fibers are then washed and dried; and Step D: conducting a non-woven cloth process comprising opening, combing, needle-bonding, calendering, and obtaining the antiseptic wound dressing of nanometer chitin calcium alginate.

A major objective of the present invention is therefore to provide an antiseptic wound dressing, through adding nanometer chitin, capable of reducing the chance of would infection.

Another objective of the present invention is, through adding nanometer chitin, the antiseptic wound dressing is able to provide superior moisture retention and enhanced wet strength, thereby achieving faster healing and convenient wound treatment.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

The present invention is an antiseptic wound dressing, comprising nanometer chitin, alkaline earth metal alginate, and antiseptic material. The nanometer chitin is tubular shaped having diameter 10~50 nm and length 20~200 nm. The amount of nanometer chitin is 0.1%~5% to the alkaline earth metal alginate.

In addition, the antiseptic material may include silver particles, Polyhexamethylene Biguanide (PHMB), or Chlorhexidine Gluconate (CHG).

Figure 1:
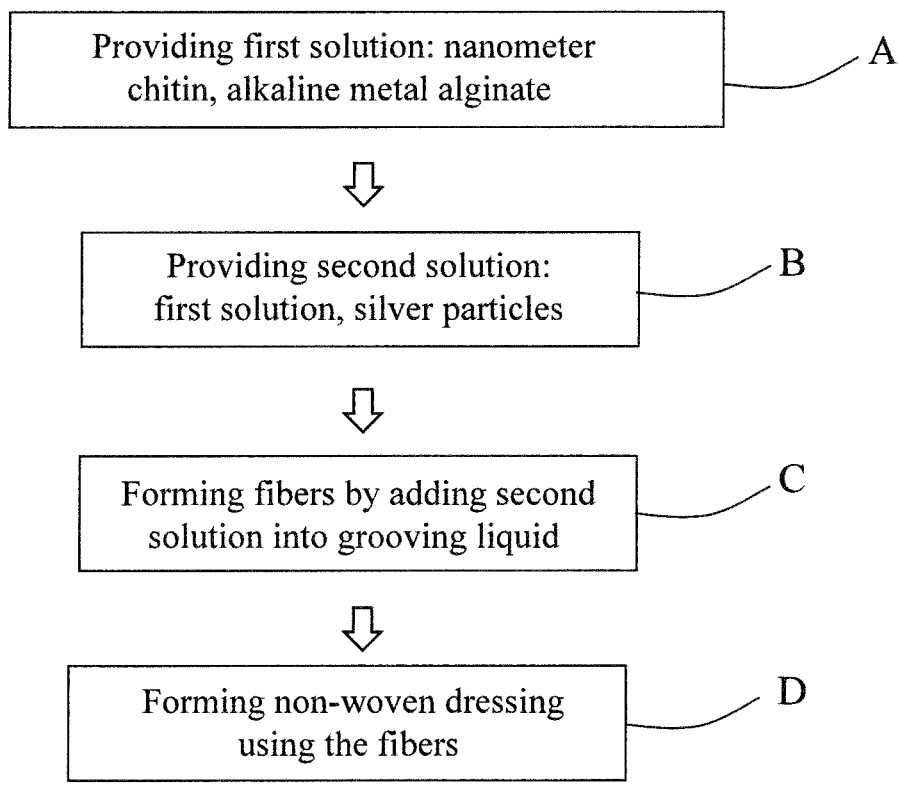
FIG. 1 is a flow diagram showing the steps of manufacturing an antiseptic wound dressing according to an embodiment of the present invention.

As shown in FIG. 1, the antiseptic wound dressing is manufactured as follows, where the antiseptic material is embodied using silver particles:

Step A: providing a first solution where nanometer chitin is dispersed evenly in water and alkaline metal alginate powder is mixed in the water.

Step B: providing a second solution by mixing silver particles in the first solution. The silver particles are added last to prevent nanometer chitin to react with the silver particles and cluster together, thereby losing its original size and function.

Step C: conducting a wet spinning process, where the second solution is filled into a grooving tank storing a grooving liquid which includes 5% calcium chloride solution. When the second solution contacts with the calcium chloride solution, the sodium ions in the alkaline metal alginate swap with calcium ions to form solid fibers of calcium alginate. The fibers are then washed and dried.

Step D: conducting a non-woven cloth process including opening, combing, needle-bonding, calendering, etc., and obtaining the antiseptic wound dressing of nanometer chitin calcium alginate.

To test the effect of the nanometer chitin in moisture retention, three wound dressings are compared: one with 100% alkaline earth metal alginate without nanometer chitin (100% Alginate), one with alkaline earth metal alginate added 1% nanometer chitin relative to the alkaline earth metal alginate (Alginate+1% chitin), and one with alkaline earth metal alginate added 2% nanometer chitin relative to the alkaline earth metal alginate (Alginate+2% chitin). Their ability of moisture retention is recorded in the Table 1.

The three wound dressings are cut into a same dimension and weighed. A fixed amount of saline solution is then added to and absorbed by the wound dressings. The wound dressings are placed in an oven whose temperature is maintained at 37 degrees Celsius. The three wound dressings are then weighed after 30, 60, 90, and 120 minutes. Their reduced weight is the amount of water lost.

TABLE 1

|  | 100% Alginate | Alginate + 1% chitin | Alginate + 2% chitin |
| --- | --- | --- | --- |
| Base weight (g) | 0.23 | 0.215 | 0.24 |
| Wet weight (g) | 2.035 | 1.84 | 2.11 |
| 30 min Water residual rate | 74% | 74% | 77% |
| 60 min Water residual rate | 64% | 66% | 70% |
| 90 min Water residual rate | 56% | 59% | 63% |
| 120 min Water residual rate | 46% | 50% | 56% |

As shown in Table 1, after 120 minutes, the Alginate+2% chitin wound dressing has 10% more remaining water than that of the 100% alginate wound dressing, suggesting that the former has superior water retention capability.

Wound healing mainly relied on the degree of moisture between wound dressing and the wound. A wound dressing having greater moisture retention capability therefore provides faster healing to the wound. In addition, a wound dressing having greater moisture retention capability requires less frequent replacement. The nanometer chitin is able to attract more water molecules due to its surface area. As shown in Table 1, the wound dressing with nanometer chitin added is superior.

To test the effect of the nanometer chitin in dressing wet strength, wound dressings of various amounts of nanometer chitin are cut into pieces of 2.54 by 7.5 cm, and tested by a universal tension machine. The result is shown in Table 2. As illustrated, wound dressings with nanometer chitin added all have superior wet strength than that of wound dressing without nanometer chitin. When wound dressing has low wet strength and it is removed from wound, portion of it may remain attach to the wound, thereby requiring additional cleaning. Therefore, wound dressing with stronger dressing wet strength is superior.

TABLE 2

| | 100% Alginate | | Alginate + 1% chitin | | Alginate + 2% chitin | |
| --- | --- | --- | --- | --- | --- | --- |
| | Tension | Average Tension | Tension | Average Tension | Tension | Average Tension |
| 1 | 9.785 | 8.2N | 15.729 | 12.35N | 13.5 | 11.74N |
| 2 | 7.278 | | 13.5 | | 11.58 | |
| 3 | 7.615 | | 9.676 | | 10.47 | |
| 4 | | | 10.525 | | 11.43 | |

Figure 2:
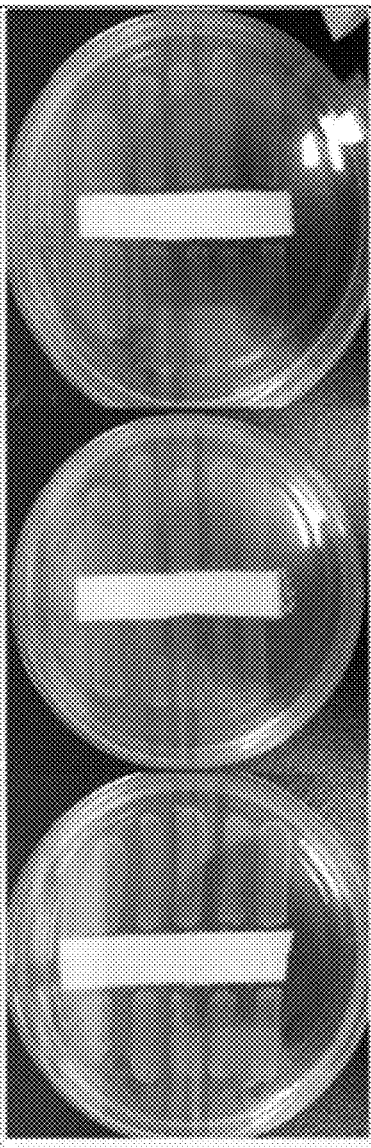
FIG. 2 provides a diagram comparing the antiseptic effect and cytotoxicity of various wound dressings.

To further test the present invention's antiseptic capability and effect on cytotoxicity, three wound dressings are compared. One wound dressing is from Coloplast, one is a conventional alkaline earth metal alginate dressing (Alginate), and one is the present invention's antiseptic wound dressing which is an alkaline earth metal alginate dressing with 1600 ppm silver (Ag) particles and 1% nanometer chitin added (relative to the alkaline earth metal alginate) added. The test result is shown in FIG. 2.

The test procedure is conducted as follows:

1. Obtaining an extract by extracting a fixed percentage of a dressing.

2. Culturing the extract and L929 cells together for 24 hours.

3. Calculating cell survival ratio, where a higher cell survival ratio indicates that the dressing is less toxic.

As shown in FIG. 2, the present invention's antiseptic wound dressing has superior antiseptic capability and low cytotoxicity. In contrast, Coloplast dressing has obvious antiseptic effect but also obvious cytotoxicity. The conventional alkaline earth metal alginate dressing (Alginate) has low cytotoxicity but inferior antiseptic effect.

As described above, the antiseptic wound dressing according to the present invention, through adding nanometer chitin, reduces the chance of would infection. In addition, nanometer chitin's ability in attracting water molecules provides superior moisture retention and enhanced wet strength, thereby achieving faster healing and convenient wound treatment.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

We claim:

1. An antiseptic wound dressing manufactured by a process comprising the steps of:
   providing a first solution where nanometer chitin is dispersed evenly in water and alkaline metal alginate powder is mixed in the water;
   providing a second solution by mixing an antiseptic material in the first solution;
   conducting a wet spinning process, where the second solution is filled into a grooving tank storing a grooving liquid which includes 5% calcium chloride solution, when the second solution contacts with the calcium chloride solution, the sodium ions in the alkaline metal alginate swap with calcium ions to form solid fibers of calcium alginate, and the fibers are then washed and dried; and
   conducting a non-woven cloth process comprising opening, combing, needle-bonding, calendering, and obtaining the antiseptic wound dressing of nanometer chitin calcium alginate;
   wherein the antiseptic wound dressing comprises nanometer chitin, alkaline earth metal alginate, and the antiseptic material;
   the nanometer chitin is tubular shaped having diameter 10~50 nm and length 20~200 nm; and
   the amount of nanometer chitin is 0.1%~5% to the alkaline earth metal alginate.

2. The antiseptic wound dressing according to claim 1, wherein the antiseptic material comprises silver particles, Polyhexamethylene Biguanide (PHMB), or Chlorhexidine Gluconate (CHG).

* * * * *